(12) United States Patent
Kukita et al.

(10) Patent No.: US 8,454,902 B2
(45) Date of Patent: Jun. 4, 2013

(54) SENSING DEVICE

(75) Inventors: Hiroyuki Kukita, Sayama (JP);
Shunichi Wakamatsu, Sayama (JP);
Wakako Shinobu, Sayama (JP)

(73) Assignee: Nihon Dempa Kogyo Co., Ltd., Tokyo (JP)

(*) Notice: Subject to any disclaimer, the term of this patent is extended or adjusted under 35 U.S.C. 154(b) by 0 days.

(21) Appl. No.: 13/369,506

(22) Filed: Feb. 9, 2012

(65) Prior Publication Data

US 2012/0219458 A1  Aug. 30, 2012

(30) Foreign Application Priority Data

Feb. 24, 2011  (JP) .................................. 2011-038937

(51) Int. Cl.
*G01N 33/00* (2006.01)
(52) U.S. Cl.
USPC ........................... 422/400; 422/82.01; 422/90
(58) Field of Classification Search
USPC ........................................ 422/82.01, 90, 400
See application file for complete search history.

(56) References Cited

U.S. PATENT DOCUMENTS 7,479,851 B2 *  1/2009  Aigner et al. ................. 333/189
8,029,741 B2 * 10/2011  Wakamatsu .................. 422/403
8,277,731 B2 * 10/2012  Yorita et al. .................... 422/82

FOREIGN PATENT DOCUMENTS

JP  2000-338022  12/2000
JP  2009-031232   2/2009

* cited by examiner

*Primary Examiner* — Sam P Siefke
(74) *Attorney, Agent, or Firm* — Jordan and Hamburg LLP

(57) ABSTRACT

A sensing device is configured that a first piezoelectric vibrator and a second piezoelectric vibrator, changing over a connection to an oscillation circuit, have the oscillation circuit in common, that an impedance of a conductive path including a first one-surface-side electrode constituting the first piezoelectric vibrator from the oscillation circuit and an impedance of a conductive path including a second one-surface-side electrode constituting the second piezoelectric vibrator from the oscillation circuit are uniform with each other, and that an impedance of a conductive path including a first other-surface-side electrode constituting the first piezoelectric vibrator from the oscillation circuit and an impedance of a conductive path including a second other-surface-side electrode constituting the second piezoelectric vibrator from the oscillation circuit are uniform with each other.

3 Claims, 15 Drawing Sheets (A)

(B)

(A)

(B)

(A)

(B)

(A)

(B)

(A)

(B)

SENSING DEVICE

BACKGROUND OF THE INVENTION

1. Field of the Invention

The present invention relates to a sensing device detecting a substance to be sensed by using a piezoelectric vibrator.

2. Description of the Related Art

As a device to perform detection and measurement of a substance to be sensed in a sample solution, there is known a sensing device using a QCM (Quarts Crystal microbalance), an outline of an example of such a sensing device being illustrated in FIG. 15. A sensing device 100 of FIG. 15 has two crystal vibrators 101, 102, and those crystal vibrators 101, 102 are formed in a common crystal piece 103. It is configured that a substance to be sensed is adsorbed to a surface of the crystal vibrator 101 and that the substance to be sensed is not absorbed to a surface of the crystal vibrator 102. Those crystal vibrators 101, 102 individually oscillate by a first oscillation circuit 104 and a second oscillation circuit 105 each connected to the respective crystal vibrators 101, 102. Outputs of the respective crystal vibrators 101, 102 are time-divided by a switch 107 and taken into a measuring part 108 of frequency, and the measuring part 108 computes a difference value of frequencies of the crystal vibrators 101, 102.

As a result of having the common crystal piece 103, the crystal vibrators 101, 102 receive an influence of disturbance such as a vibration outside the device similarly to each other. Thus, the computed difference value of frequency reflects a frequency change due to absorption of the substance to be sensed, and detection and measurement of the substance to be sensed have been performed based on the difference value.

Incidentally, in a biochemistry examination of a hospital or an investigation by a reagent manufacturer, there is a demand for performing measurement of a substance to be sensed contained in a sample solution having a comparatively high viscosity. More specifically, an investigation is being carried on in which, for example, human saliva is taken and detection and measurement of markers of various diseases contained in the saliva are performed thereby to diagnose the disease of a patient. It is considered to use the above-described sensing device 100 for performing such an investigation.

It is found, however, that if the sensing device 100 performs measurement of a sample solution with a high viscosity, change amounts of frequency due to viscosities are different in the one crystal vibrator and in the other crystal vibrator, leading to an apprehension that a measurement accuracy is reduced as a result. This is because a difference in impedances of conductive paths from the oscillation circuits 104, 105 to electrodes formed in the crystal piece 103 emerges as a difference in a value of a crystal impedance (CI) to be a value of C0 or R1 at a time that the crystal vibrator is viewed in an equivalent circuit, and it is because even if a slight difference exists in a characteristic of each circuit between the oscillation circuits 104, 105, that difference is reflected.

Patent Document 1 describes a sensing sensor in which a plurality of vibrators are provided in one crystal piece, and lengths of conductive paths from oscillation circuits to respective vibrators are different from each other, and thus the above-described problem cannot be solved. Further, Patent Document 2 describes that one oscillation circuit is used for a plurality of vibrators and that a connection is temporally switched, but a means for solving the above-described problem is not described.

[Patent Document 1] Japanese Patent Application Laid-open No. 2000-338022

[Patent Document 2] Japanese Patent Application Laid-open No. 2009-31232

SUMMARY OF THE INVENTION

The present invention is made in view of the above circumstances, and its object is to provide a technique enabling highly accurate detection of a substance to be sensed in a sample solution.

A sensing device of the present invention is a sensing device using a piezoelectric vibrator whose characteristic vibration number changes by absorption of a substance to be sensed contained in a sample solution and sensing the substance to be sensed by a change of the characteristic vibration number, the sensing device including:

a first piezoelectric vibrator configured to be provided with a first one-surface-side excitation electrode on one of a front surface and a rear surface of a first vibration area provided in a piezoelectric piece and a first other-surface-side excitation electrode on the other, respectively, and configured that the substance to be sensed is absorbed;

a second piezoelectric vibrator configured to be provided with a second one-surface-side excitation electrode on one of a front surface and a rear surface of a second vibration area provided in the piezoelectric piece and a second other-surface-side excitation electrode on the other, respectively, and configured that the substance to be sensed is not absorbed;

a switching part switching the first one-surface-side excitation electrode and the second one-surface-side excitation electrode each other to connect to a subsequent stage side;

an oscillation circuit common to the first piezoelectric vibrator and the second piezoelectric vibrator, the oscillation circuit connected to the first other-surface-side excitation electrode and the second other-surface-side excitation electrode and provided in a subsequent stage of the switching part, and making the first piezoelectric vibrator and the second piezoelectric vibrator oscillate time-dividedly; and a measuring part provided in a subsequent stage of the oscillation circuit, and taking in outputs from the first piezoelectric vibrator and the second piezoelectric vibrator and measuring the characteristic vibration numbers of the first piezoelectric vibrator and the second piezoelectric vibrator, respectively, wherein an impedance of a conductive path including the first one-surface-side excitation electrode and an impedance of a conductive path including the second one-surface-side excitation electrode, when viewed from the oscillation circuit toward the first one-surface-side excitation electrode and the second one-surface-side excitation electrode, respectively, are uniform with each other, and wherein an impedance of a conductive path including the first other-surface-side excitation electrode and an impedance of a conductive path including the second other-surface-side excitation electrode, when viewed from the oscillation circuit toward the first other-surface-side excitation electrode and the second other-surface-side excitation electrode, respectively, are uniform with each other.

For example, the impedance of the conductive path and the impedance of the conductive path being uniform with each other means that a difference between the impedances of the respective conductive paths is equal to or less than 3%, and, for example, the switching part receives a switching signal outputted from a switching signal output part and changes over the connection of the first piezoelectric vibrator and the second piezoelectric vibrator to the subsequent stage side each other, and the measuring part validates a measured value of the characteristic vibration number after passage of a time set in advance since the output of the switching signal. The difference between the impedances of the conductive paths being 3% means that when the impedance of the conductive path with the larger impedance is defined as 100%, the impedance of the conductive path with the smaller impedance is 97%.

According to the sensing device of the present invention, it is configured that an impedance of a conductive path including an electrode of a first piezoelectric vibrator from an oscillation circuit which is common between the piezoelectric vibrators and an impedance of a conductive path including an electrode of a second piezoelectric vibrator from the oscillation circuit are uniform with each other. By such a configuration, since a characteristic of a circuit from the oscillation circuit to the first piezoelectric vibrator and a characteristic of a circuit from the oscillation circuit to the second piezoelectric vibrator are uniform, dispersion between a change of a characteristic vibration number of the first piezoelectric vibrator and a change of a characteristic vibration number of the second piezoelectric vibrator is suppressed even in a case of a sample solution with a high viscosity, so that detection of a substance to be sensed can be performed with a high accuracy.

DETAILED DESCRIPTION OF THE PREFERRED EMBODIMENT(S)

Figure 1:
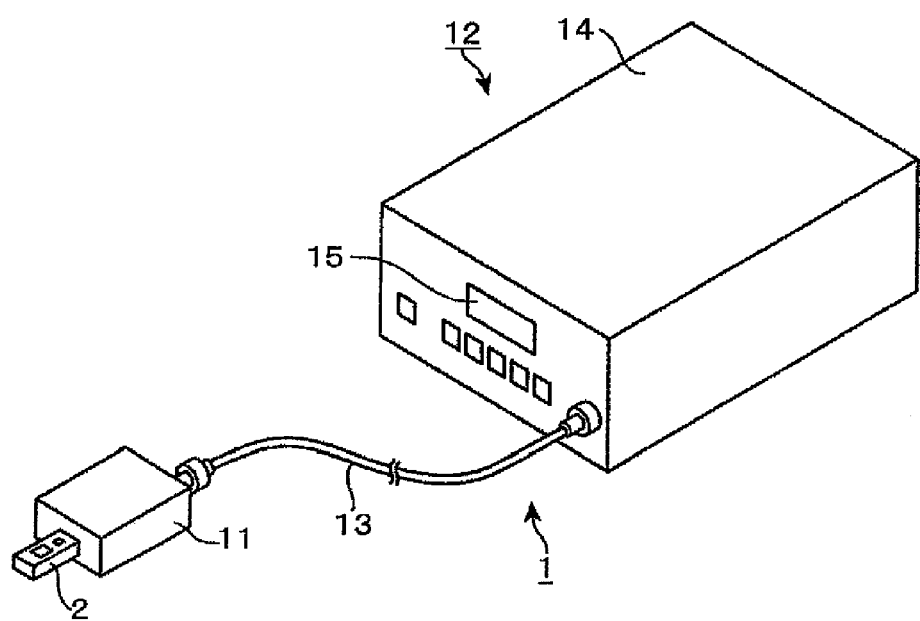
FIG. 1 is an external appearance configuration view of a sensing device according to the present invention.

Hereinafter, a sensing device 1 for implementing a sensing method of the present invention will be described. The sensing device 1 performs measurement of chromogranins as a substance to be sensed, chromogranins being a stress marker contained in human saliva being a sample solution. As shown in an external appearance configuration view of FIG. 1, the sensing device 1 has an oscillation circuit unit 11 and a measuring part 12, the oscillation circuit unit 11 being attachably/detachably connected to the measuring part 12 via a cable 13. A display part 15 provided in a front surface of a casing 14 of the measuring part 12 is constituted by, for example, an LED display screen or a liquid crystal display screen, and displays a measurement result such as a frequency or an amount of change of frequency.

Figure 2:
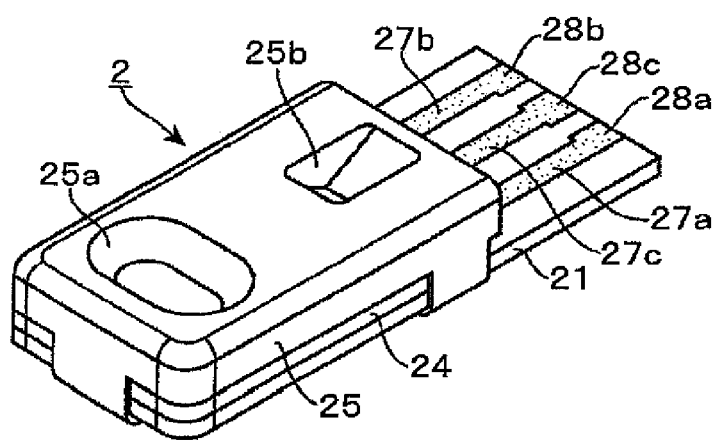
FIG. 2 is a perspective view of a sensing sensor constituting the sensing device.
Figure 3:
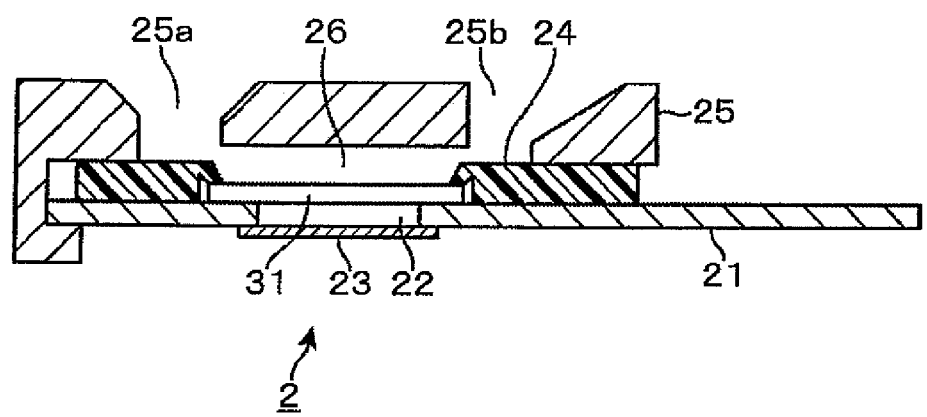
FIG. 3 is a vertical cross-sectional side view of the sensing sensor.

A sensing sensor 2 is attachably/detachably connected to the oscillation circuit unit 11. FIG. 2 shows a perspective view of the sensing sensor 2, and FIG. 3 shows a vertical cross-sectional side view of the sensing sensor 2, respectively. A through hole 22 is formed in one end side of a substrate 21 constituting the sensing sensor 2, and a later-described crystal piece 31 is provided in a manner to block up the through hole 22. It is configured that the through hole 22 is blocked up by a sheet 23 from a rear surface side of the substrate 21, and that, from a front surface side of the substrate 21, a sheet 24 and an upper cover case 25 are stacked in this order from the bottom. By the above configuration, the through hole 22 is formed as an airtight space, so that the sensing sensor 2 of a Langevin type is constituted. Further, a peripheral edge of the crystal piece 31 is pressed by the sheet 24, and the crystal piece 31 is fixed to the substrate 21.

The upper cover case 25 is provided with an injection port 25a of a sample solution and an observation port 25b of the sample solution, and as a result that the sample solution is injected from the injection port 25a, the sample solution is filled in a storage space 26 in an upper surface side of the crystal piece 31, the storage space 26 formed by a through hole provided in the sheet 24.

Figure 4:
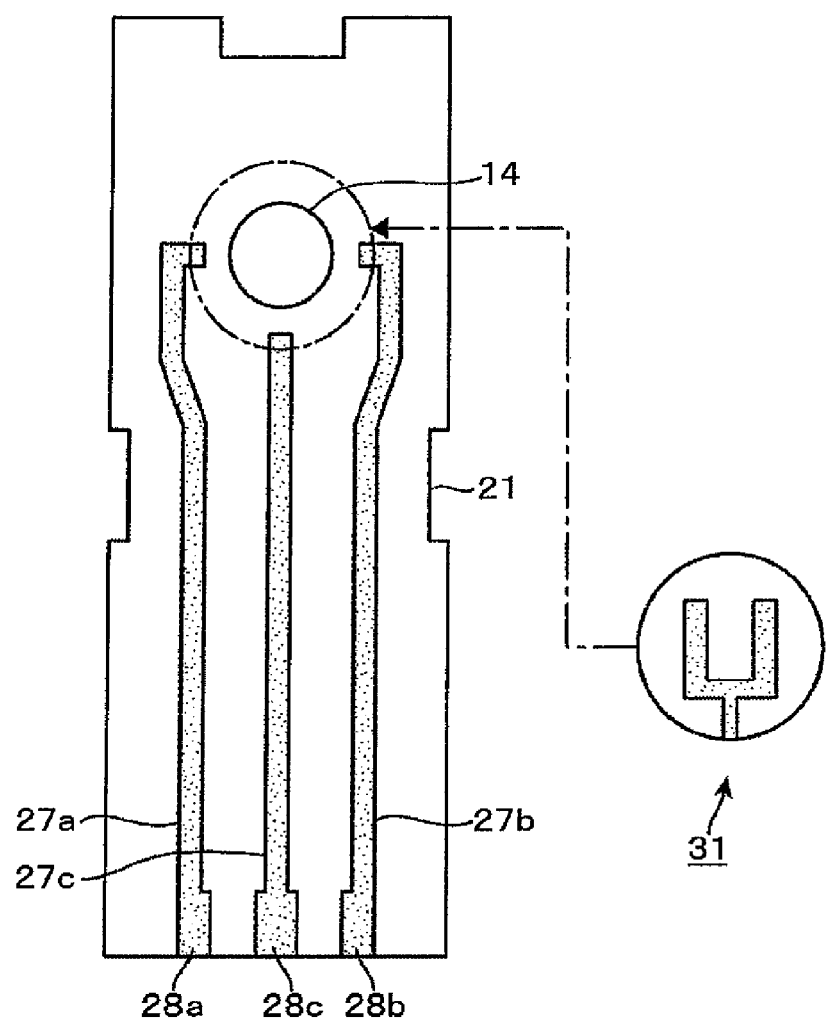
FIG. 4 is a plan view of a substrate constituting the sensing sensor.

FIG. 4 shows a front surface of the substrate 21. The substrate 21 is provided with linear electrode films 27a, 27b, 27c extending from the other end in a longitudinal direction to the one end side, and the other end sides of the respective electrode films 27a to 27c are widened and configured as connecting terminals 28a to 28c. The electrode films 27a to 27c are formed to have the same width and the same film thickness as one another, and are constituted by the same material as one another, for example, gold. Further, the electrode films 27a, 27b are formed to have shapes symmetrical at a width center of the substrate 21, and have the same length. Thereby, the electrode films 27a, 27b have the same impedance as each other.

Figure 5:
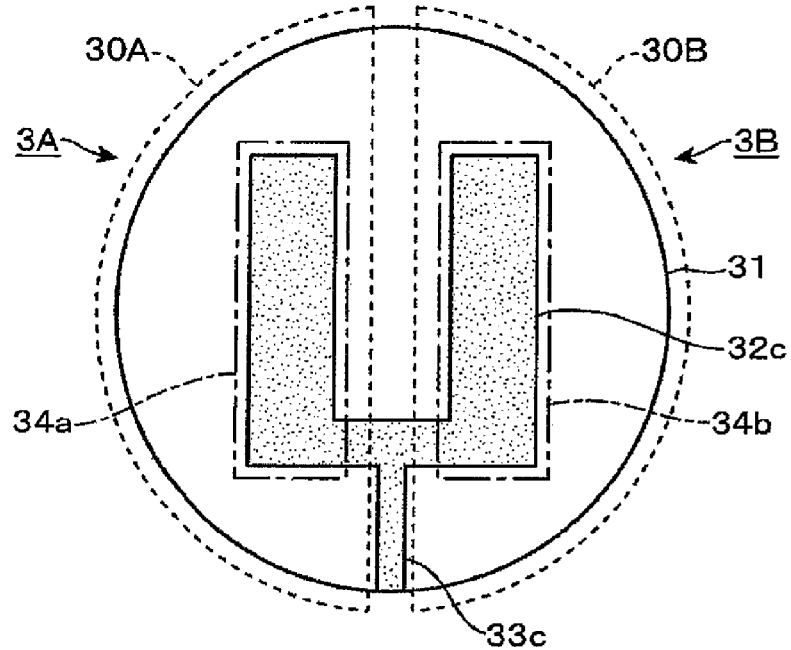
FIG. 5A and FIG. 5B are plan views of a crystal vibrator constituting the sensing sensor.
Figure 5:
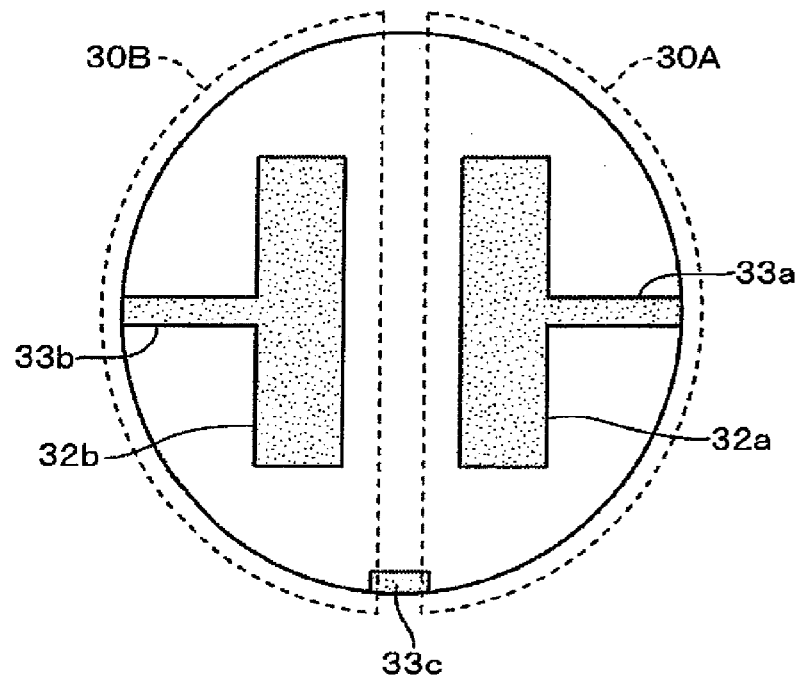

The crystal piece 31 will be described with reference to FIG. 5A and FIG. 5B showing its front surface and rear surface, respectively. The crystal piece 31 is, for example, circular, and has a first vibration area 30A and a second vibration area 30B which vibrate independently of each other. The first vibration area 30A constitutes a first crystal vibrator 3A, and the second vibration area 30B constitutes a second crystal vibrator 3B. On the front surface of the crystal piece 31 is formed an excitation electrode 32c having a U-shape. An electrode 33c is drawn out from the excitation electrode 32c in an opposite direction to an opening direction of the U-shape toward a peripheral portion of the crystal piece 31, and the electrode 33c is routed around a rear surface side via a side end surface of the crystal piece 31. Further, in FIG. 5A, in the excitation electrode 32c, an area facing a later-described excitation electrode 32a is defined as an area 34a and an area facing an excitation electrode 32b is defined as an area 34b, which are indicated by being circled by chain lines, respectively.

Further, in the rear surface of the crystal piece 31, the excitation electrode 32a is provided in the first vibration area 30A, and the excitation electrode 32b is provided in the second vibration area 30B. The respective excitation electrodes 32a, 32b are formed to be rectangular and are provided to face the excitation electrode 32c. Electrodes 33a, 33b are drawn out from the excitation electrodes 32a, 32b respectively, toward edge portions of the crystal piece 31.

In a front side and a rear side of the crystal piece 31, layouts of the right and left electrodes are configured similarly, and film thicknesses of the respective electrodes are even. Thereby, an impedance of a conductive path from the electrode 33c to the area 34a of the excitation electrode 32c and an impedance of a conductive path from the electrode 33c to the area 34b of the excitation electrode 32c are configured to be equal, and an impedance of a conductive path from the electrode 33a to the excitation electrode 32a and an impedance of a conductive path from the electrode 33b to the excitation electrode 32b are configured to be equal. In a scope of claims, the excitation electrode 32a is equivalent to a first one-surface-side excitation electrode, the excitation electrode 32b is equivalent to a second one-surface-side excitation electrode, the area 34a is equivalent to a first other-surface-side excitation electrode, and the area 34b is equivalent to a second other-surface-side electrode. As shown in FIG. 4, the electrodes 33a, 33b, 33c are electrically connected to the electrode films 27a, 27b, 27c of the substrate 21, respectively.

Figure 6:
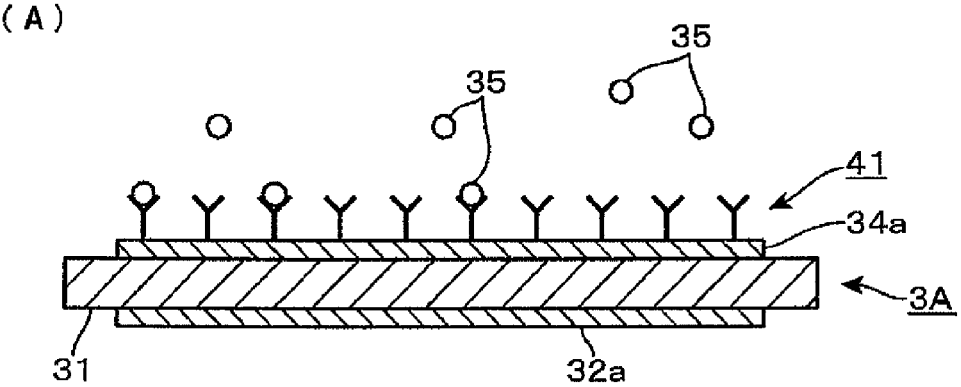
FIG. 6A and FIG. 6B are vertical cross-sectional side views of the crystal vibrator.
Figure 6:
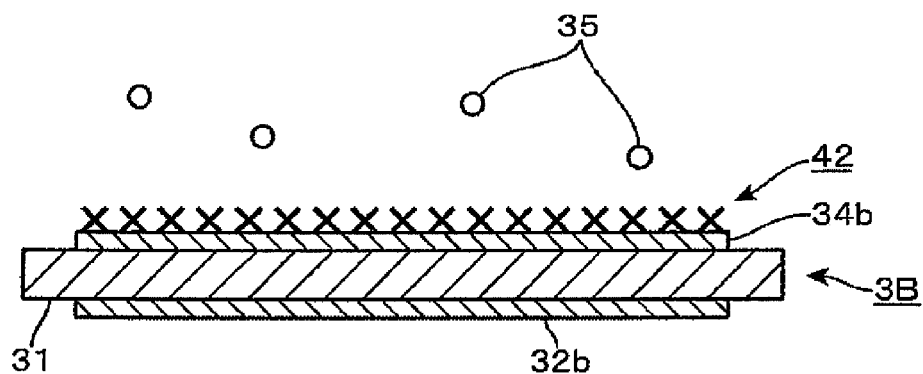

FIG. 6A and FIG. 6B schematically show a side surface of the first crystal vibrator 3A and a side surface of the second crystal vibrator 3B, respectively. An absorption film 41 is formed in a front surface of the area 34a of the excitation electrode 33c of the first crystal vibrator 3A. The absorption film 41 absorbs chromogranins being a substance 35 to be sensed by, for example, an antigen-antibody reaction. Further, an absorption obstructing film 42 is formed in a front surface of the area 34b of the excitation electrode 33c of the second crystal vibrator 3B, so that the chromogranins is not absorbed.

Figure 7:
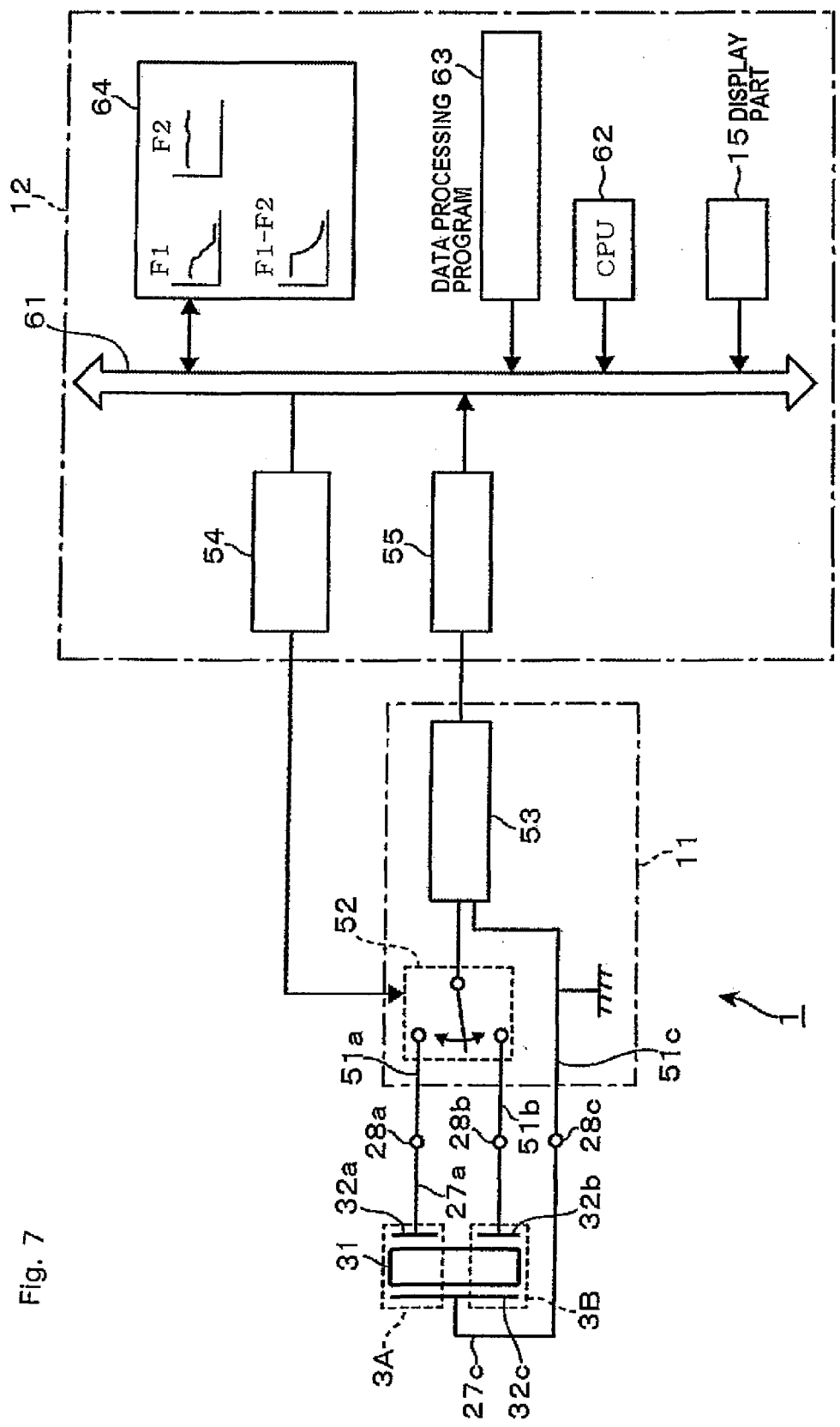
FIG. 7 is a block diagram showing a configuration of the sensing device.

FIG. 7 is a block diagram of the sensing device 1, and the oscillation circuit unit 11 constituting the sensing device 1 will be described with reference to FIG. 7. An end portion of the substrate 21 is attachably/detachably inserted into a slot provided in the oscillation circuit unit 11, and conductive paths 51a, 51b, 51c are formed inside the slot. When the substrate 21 is inserted into the slot, the connecting terminals 28a, 28b, 28c of the substrate 21 are connected to the conductive paths 51a, 51b, 51c, respectively. The conductive paths 51a, 51b, 51c are constituted by, for example, electrode films patterned on a substrate, similarly to the connecting terminals 28a to 28c.

The conductive paths 51a, 51b, having the same film thickness and being formed to have the same length and the same width as each other similarly to the electrode films 27a, 27b, for example, are formed to have similar impedances from one end to the other end thereof. A switch 52 is connected in a subsequent stage of the conductive paths 51a, 51b. The conductive path 51c is connected to an oscillation circuit 53 and is grounded.

In a subsequent stage of the switch 52, the oscillation circuit 53 is provided. The switch 52 changes over a connection to the oscillation circuit 53 between the excitation electrodes 32a, 32b, in correspondence with a switching signal outputted from a switching signal output part 54. When the oscillation circuit 53 is connected to the excitation electrode 32a, the first crystal vibrator 3A oscillates by the oscillation circuit 53, and when the oscillation circuit 53 is connected to the excitation electrode 32b, the second crystal vibrator 3B oscillates by the oscillation circuit 53. In this way, the first crystal vibrator 3A and the second crystal vibrator 3B oscillate alternately, and frequency signals from the respective crystal vibrators 3A, 3B are taken into a subsequent stage time-dividedly. Thereby, the later-described measuring part 12 can obtain oscillation frequencies of the respective crystal vibrators 3A, 3B concurrently. When an output from the first crystal vibrator 3A is defined as a channel 1 (F1) and an output from the second crystal vibrator 3B is defined as a channel 2 (F2), it is configured that the connection is changed over, for example, every 1/n second, that the oscillation frequencies of the respective channels are taken into the subsequent stage, and that the frequencies of the respective channels can be obtained simultaneously in practice.

As a result that the oscillation circuit 53 and a previous stage side of the oscillation circuit 53 are configured as above, it is configured that, when viewed from the oscillation circuit 53, an impedance of a conductive path to the excitation electrode 32a including the excitation electrode 32a via the switch 52 and an impedance of a conductive path to the excitation electrode 32b including the excitation electrode 32 via the switch 52 are equal to each other. Further, it is configured that an impedance of a conductive path viewed from the oscillation circuit 53 to the area 34a of the excitation electrode 32c and an impedance of a conductive path viewed from the oscillation circuit 53 to the area 34b of the excitation electrode 32c are equal to each other. Further, since the oscillation circuit 53 is made common between the first crystal vibrator 3A and the second crystal vibrator 3B, circuit characteristics of the oscillation circuit are uniform when viewed from the respective crystal vibrators.

Subsequently, the measuring part 12 will be described. The measuring part 12 has a measuring circuit part 55. The measuring circuit part 55 is provided in the subsequent stage of the oscillation circuit 53, and digitally processes the frequency signal being an input signal and output to a subsequent stage. Further, the measuring part 12 has a data bus 61, and to the data bus 61 are connected a CPU 62, a storage unit storing a data processing program 63, the aforementioned switching signal output part 54, the measuring circuit part 55, and the aforementioned display part 15.

The data processing program 63 obtains time-series data of an oscillation frequency "F1" of the first crystal vibrator 3A and time-series data of an oscillation frequency "F2" of the second crystal vibrator 3B based on a signal outputted from the measuring circuit part 55, and stores in a memory 64. Further, simultaneously with such a data acquisition operation, a difference "F1−F2" between the respective time-series data of the oscillation frequency F1 acquired from the channel 1 and of the oscillation frequency F2 acquired from the channel 2 at the same time zone is each computed and time-series data of the difference data is acquired to be stored in the memory 64, and a graph of change with time of the "F1−F2" is displayed in the display part 15.

Next, process steps for judging existence/absence of a substance to be sensed contained in human saliva as described above by using the sensing device 1 will be explained. First, when the measuring part 12 is activated and the sensing sensor 2 is inserted into the slot of the oscillation circuit unit 11, by changeover of the switch 52 in correspondence with an output of a switching signal, a connection among the first crystal vibrator 3A, the second crystal vibrator 3B, and the oscillation circuit 53 is changed over, so that the crystal vibrator connected to the oscillation circuit 53 oscillates, frequency signals F1, F2 corresponding to respective frequencies are outputted into the subsequent stage alternately. Then, the respective frequency signals F1, F2 are taken into the measuring circuit part 55 and A/D converted, and thereafter, each digital value is outputted into the subsequent stage.

Figure 8:
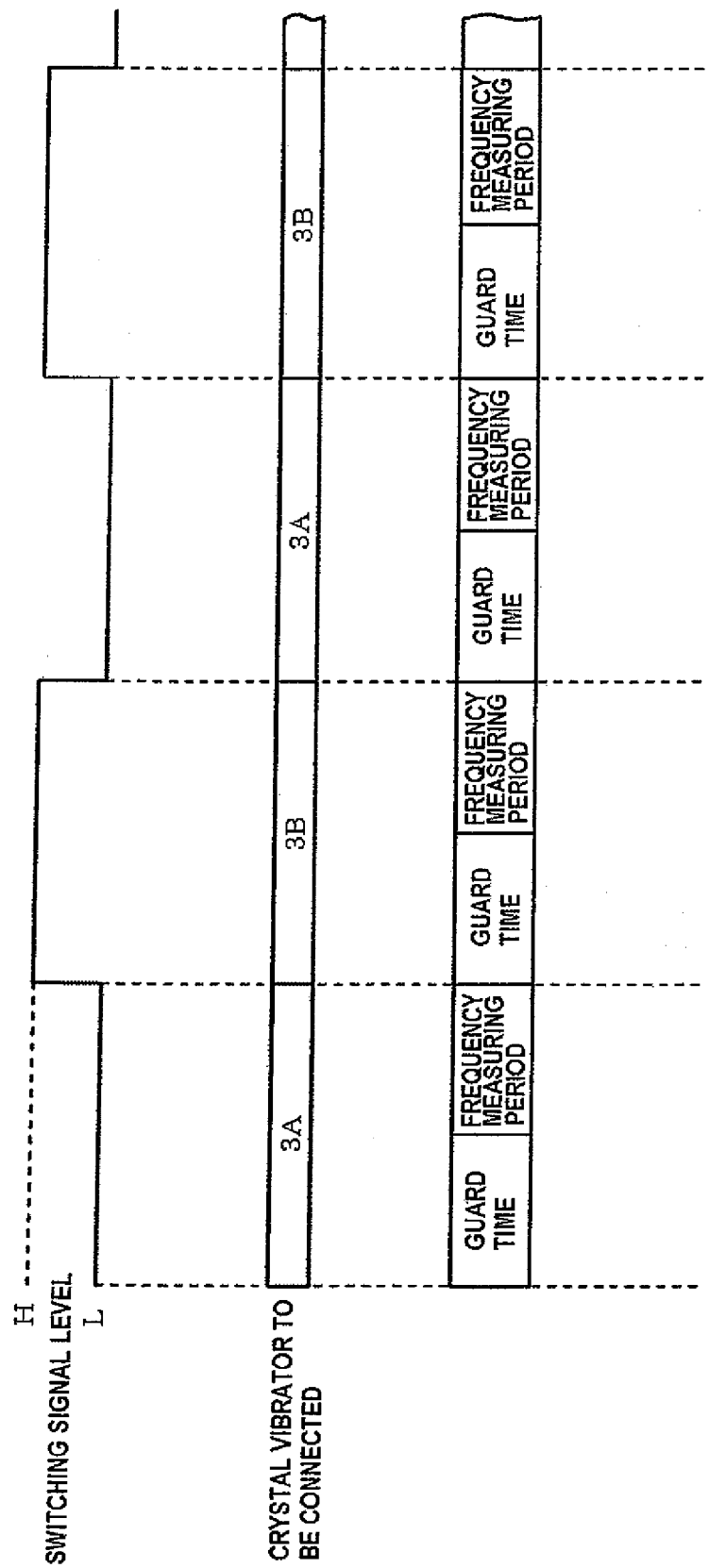
FIG. 8 is a time chart showing a timing at which a frequency is measured.

Incidentally, FIG. 8 is a time chart showing a relation between an output level of a switching signal and a crystal vibrator connected in correspondence with the output level, and the output level changes over between L and H at a predetermined cycle. When the output level is L, the first crystal vibrator 3A is connected to the oscillation circuit 53, and when the output level is H the second crystal vibrator 3B is connected to the oscillation circuit 53. As shown in a later-described experiment, during a predetermined time, for example, during 1 msec, from a point of time at which the switch signal level changes over between L and H, oscillation of the crystal vibrators 3A, 3B becomes unstable, and thus measurement of the frequency is not performed in the measuring part 12. In FIG. 8, a period in which measuring of the frequency is not performed as above is represented as a guard time. When the guard time passes, the measuring part 12 measures the frequencies of the respective frequency signals F1, F2. It should be noted that in the scope of claims, an instant at which the switching signal changes over from L to H and an instance at which the switching signal changes over from H to L are defined as output times of the switching signals.

The frequencies "F1, F2" of the respective channels having been measured are stored in the memory 64, and further, based on the stored "F1, F2", "F1−F2" is computed and stored in the memory 64, such an operation being continued. Further, the aforementioned graph is displayed in the display part 15, and the change of the frequency difference "F1−F2" is displayed in real time.

Next, a user drops a sample solution to the injection port 25a of the sensing sensor 2. Thereby, an environmental atmosphere of the front surfaces of the first crystal vibrator 3A and the second crystal vibrator 3B are changed from a gas phase to a liquid phase, and the first crystal vibrator 3A and the second crystal vibrator 3B receive a mass addition effect based on a hydraulic pressure. On this occasion, as described above, it is constituted that the impedance of the conductive path from the oscillation circuit 53 to the excitation electrode 32a and the impedance of the conductive path from the oscillation circuit 53 to the excitation electrode 32b are equal and it is constituted that the impedance from the oscillation circuit 53 to the area 34a of the excitation electrode 33c and the impedance from the oscillation circuit 53 to the area 34b of the excitation electrode 33c are equal to each other, and thus the circuit viewed from the oscillation circuit 53 toward the first crystal vibrator 3A and the circuit viewed from the oscillation circuit 53 toward the second crystal vibrator 3B are practically the same in the characteristics. Therefore, irrespective of a viscosity of the sample solution, the oscillation frequency F1 from the first crystal vibrator 3A and the oscillation frequency F2 from the second crystal vibrator 3B are reduced similarly to each other.

Figure 9:
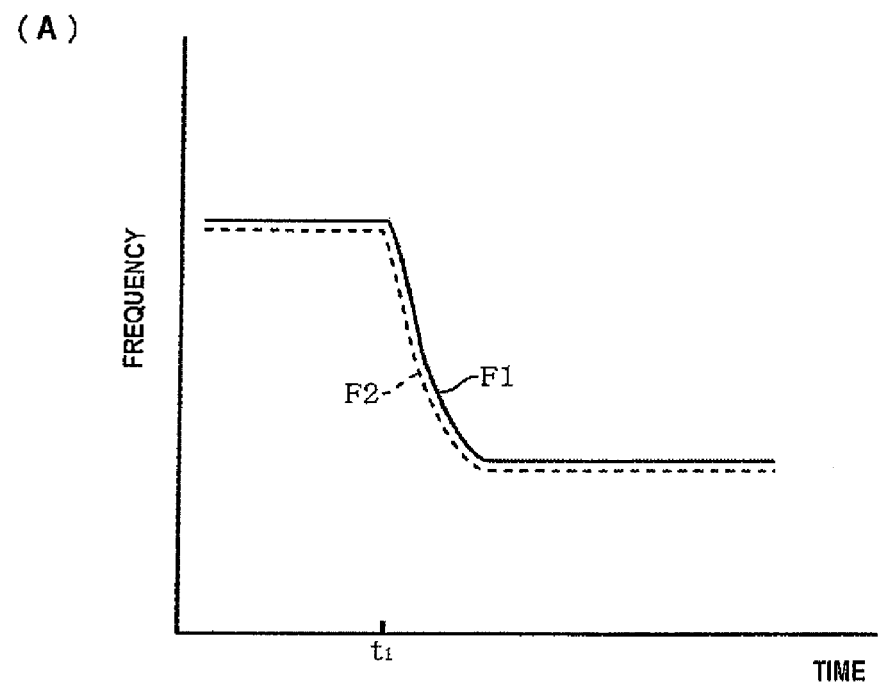
FIG. 9A and FIG. 9B are graphs showing states in which a frequency changes.
Figure 9:
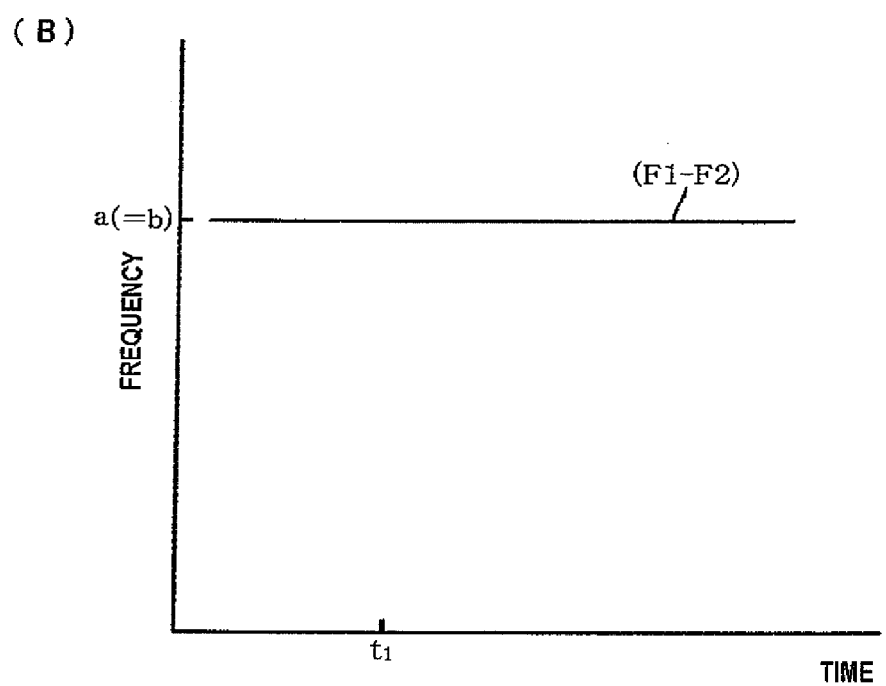

If the sample solution does not contain a substance to be sensed, the above-described absorption of the substance to be sensed does not occur in the first crystal vibrator 3A, and the frequencies F1, F2 which change in correspondence with a temperature or a viscosity of the sample solution are taken out from the channel 1 and the channel 2. Therefore, as shown in a graph of FIG. 9A, the oscillation frequencies F1, F2 are reduced uniformly with each other, and as indicated in FIG. 9B, the frequency difference F1−F2 hardly changes.

Figure 10:
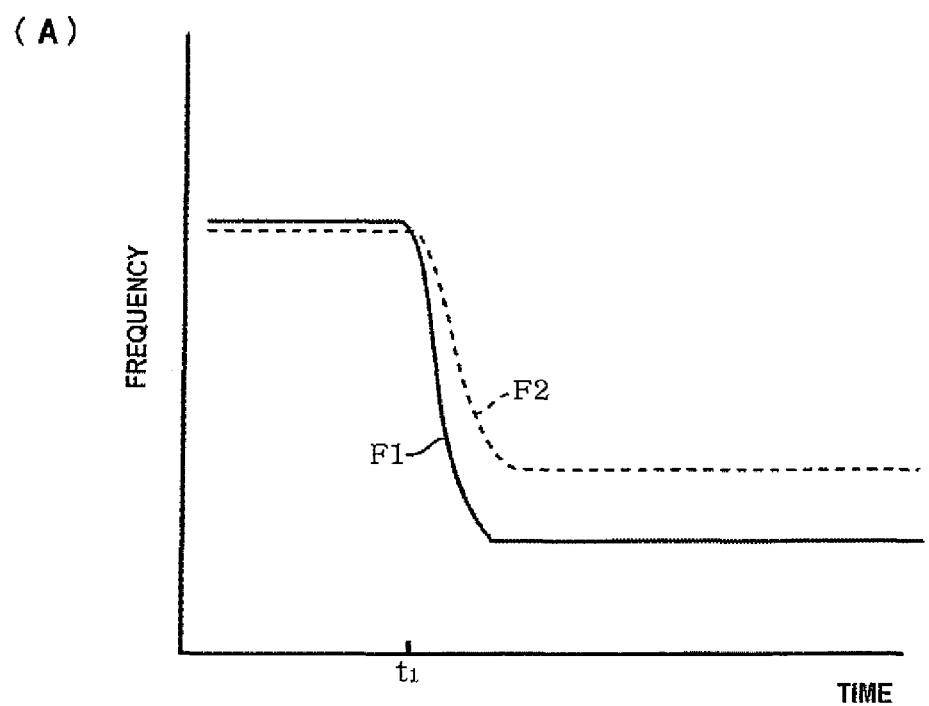
FIG. 10A and FIG. 10B are graphs showing states in which a frequency changes.
Figure 10:
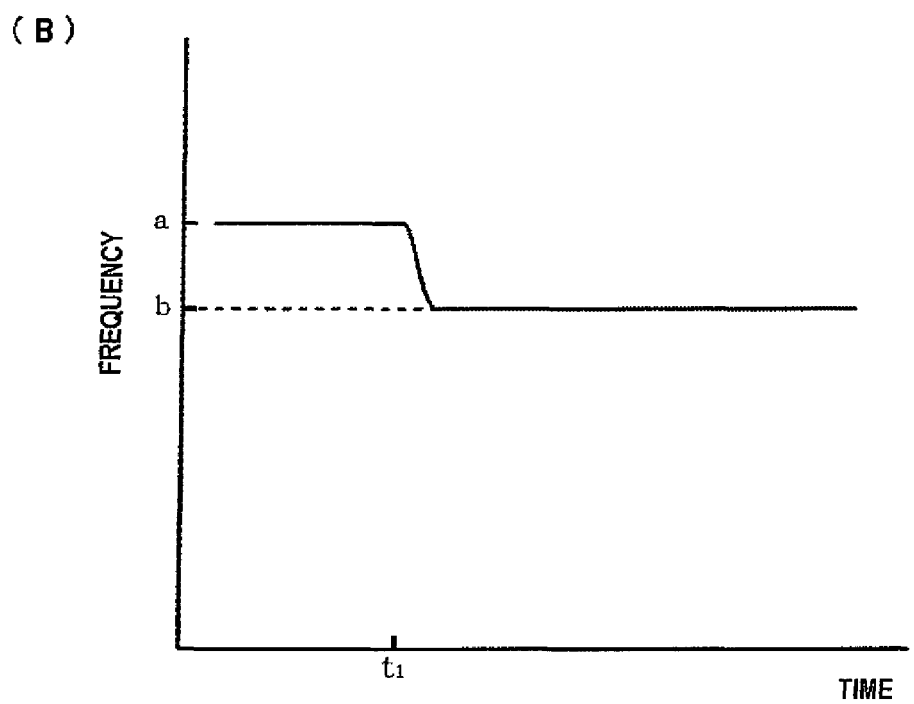

If the substance to be sensed is contained in the sample solution, the substance to be sensed in the sample solution is absorbed to the front surface of the first crystal vibrator 3A, but the substance to be sensed is not absorbed to the front surface of the second crystal vibrator 3B, and thus a mass addition effect the first crystal vibrator 3A receives becomes large compared with the second crystal vibrator 3B, and consequently, as shown in a graph of FIG. 10A, the oscillation frequency F1 is substantially reduced compared with the oscillation frequency F2, and as shown in the graph of FIG. 10B, the frequency difference "F1−F2" becomes large. It should be noted that in the graphs of FIG. 9A, FIG. 9B, FIG. 10A, and FIG. 10B, a time t1 indicates a timing to inject the sample solution into the sensing sensor 2.

The user calculates a difference value a−b between a value a of "F1−F2" before supply of the sample solution and a value b of "F1−F2" after supply of the sample solution, and if the difference value a−b is within a predetermined permissible value, it is judged that the substance to be sensed does not exist in the sample solution, and if the difference value a−b exceeds the permissible value, it is judged that the substance to be sensed exists in the sample solution.

As described above, in the sensing device 1, the oscillation circuit 53 is made common between the first crystal vibrator 3A and the second crystal vibrator 3B, it is constituted that the impedance of the conductive path from the oscillation circuit 53 to the excitation electrode 32a of the first crystal vibrator 3A and the impedance of the conductive path to the excitation electrode 32b are equal, and it is constituted that the impedance from the oscillation circuit 53 to the area 34a of the excitation electrode 33c and the impedance from the oscillation circuit 53 to the area 34b of the excitation electrode 33c are equal to each other. Thereby, it is prevented that a difference of the characteristics between the oscillation circuits brought about by individually providing an oscillation circuit 53 per a crystal vibrator influences frequencies of respective channels, and it is suppressed that dispersion of characteristics occurs between a circuit viewed from the oscillation circuit 53 to the first crystal vibrator 3A and a circuit viewed from the oscillation circuit 53 to the second crystal vibrator 3B. As a result, an occurrence of dispersion between an oscillation frequency F1 and an oscillation frequency F2 due to a viscosity of a sample solution can be suppressed, so that it is possible to perform measurement of a substance to be sensed at a high accuracy based on a frequency difference F1−F2.

Further, in the sensing device 1, since a frequency outputted in a state that oscillation is not stable immediately after the switch 52 is changed over is not measured, it is possible to measure the oscillation frequencies F1, F2 at a higher accuracy, so that measurement of a substance to be sensed can be performed more securely.

Incidentally, in a conventional sensing device, since two crystal vibrators are formed in a common crystal piece, in order to prevent vibrations of the respective crystal vibrators from interfering with each other to deteriorate frequency stability, excitation electrodes are provided distantly from each other on the crystal piece, film thicknesses of the crystal piece and the excitation electrodes are changed between the crystal vibrators to stagger frequencies, for example, or a driving electric power for making a crystal oscillate is reduced. However, in the above-described sensing device 1, since the first crystal vibrator 3A and the second crystal vibrator 3B are made to oscillate time-dividedly, it is possible to suppress interference of a vibration of one crystal vibrator with a vibration of the other crystal vibrator. Accordingly, it is unnecessary to adjust a film thickness of a crystal piece and electrodes as above, and the number of process steps for manufacturing a sensing sensor 2 can be reduced and flexibility of disposition of an excitation electrode in a crystal piece becomes high. Further, the driving electric power can be increased, and thus an oscillation margin can be increased. Further, since an oscillation circuit is made common for the crystal vibrators 3A, 3B, the number of components of the sensing device 1 can be reduced than in a case that an oscillation circuit is provided per a crystal vibrator, so that reduction of a manufacturing cost and down-sizing of the sensing device 1 can be contrived.

Further, in the above-described example, though existence/absence of the substance to be sensed in the sample solution is detected, it is also possible to acquire a relational expression between the above-described amount of change (a−b) of the oscillation frequency difference "F1−F2" and a density of a substance to be sensed in a sample solution in advance thereby to find a density of the substance to be sensed in the sample solution from the relational expression and the amount of change (a−b) obtained by measurement. Further, though it is configured that in the above-described example the sensing sensor is kept in a standstill state after a predetermined amount of sample solution is dropped, a configuration is possible as what is called a flow-cell sensing sensor in which a sample solution is continuously supplied to front surfaces of crystal vibrators 3A, 3B by a pump or the like and the sample solution is continuously discharged from the front surfaces of the crystal vibrators 3A, 3B thereby to distribute the sample solution from one edge to the other edge of a crystal piece.

It is configured that the impedance of the conductive path from the oscillation circuit 53 to the excitation electrode 32a and the impedance of the conductive path from the oscillation circuit 53 to the excitation electrode 32b are equal and it is configured that the impedance from the oscillation circuit 53 to the area 34a of the excitation electrode 33c and the impedance from the oscillation circuit 53 to the area 34b of the excitation electrode 33c are equal as described above, whereby the change of the frequencies F1 and F2 can be made uniform under the same environment, but even if the respective impedances are not equal as above, as long as the impedances are close and uniform with each other, dispersion of the frequencies F1, F2 due to a viscosity of a sample solution can be suppressed. For example, if a difference between the respective impedances is equal to or less than 3%, such an effect can be obtained. In other words, for example, when the larger impedance is defined as 100%, the smaller impedance is 97% to 100%.

Figure 11:
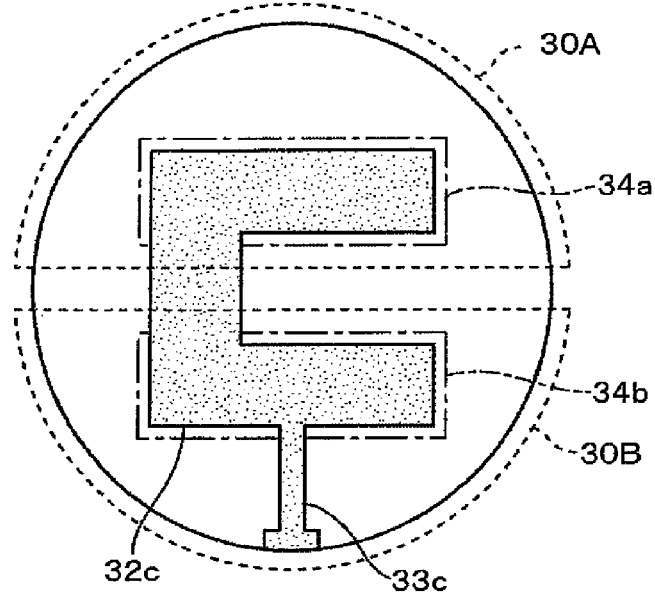
FIG. 11A and FIG. 11B are plan views showing another configuration of a crystal vibrator.
Figure 11:
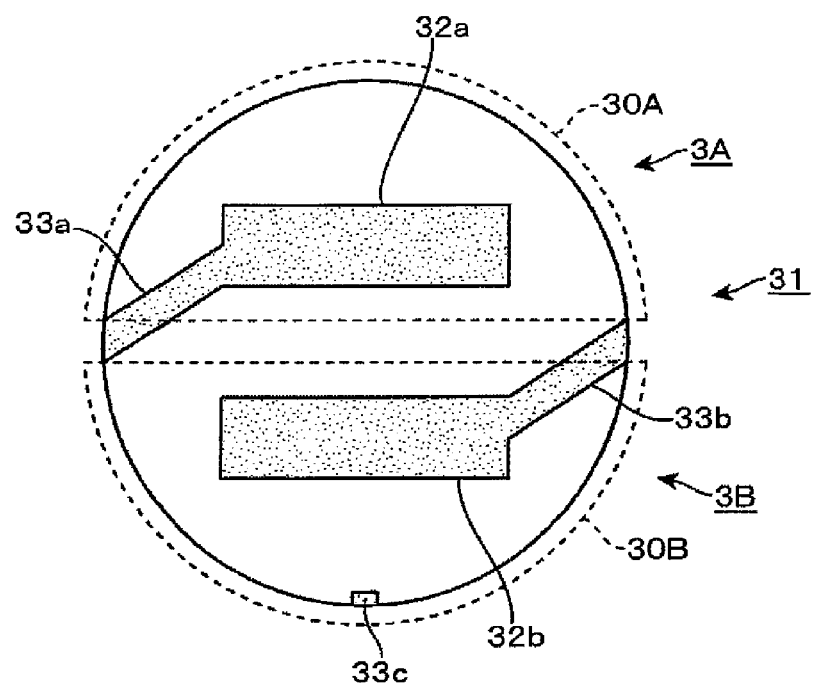

Accordingly, as a layout of electrodes of a crystal piece 31, a configuration as shown in FIG. 11A and FIG. 11B is possible. FIG. 11A shows a front surface side of the crystal piece 31, while FIG. 11B shows a rear surface side of the crystal piece 31. The crystal piece 31 is configured that, similarly to in the aforementioned example, electrodes 33a to 33c are connected to electrode films 27a to 27c when the crystal piece 31 is mounted on a substrate 21. A difference from the above-described example in the crystal piece 31 is that the electrode 33c is drawn out to be orthogonal to an opening direction of a U-shape of an excitation electrode 32c. Therefore, an impedance to an area 34a of an excitation electrode 32c and an impedance to an area 34b of the excitation electrode 32c, when viewed from an oscillation circuit 53, are different from each other, but as long as a difference of the impedances is within the above-described range, an effect similar to that in a case of configuring the crystal piece 31 as in FIG. 5 can be obtained.

(Evaluation Test)

An evaluation test performed in relation to the present invention will be described. In each evaluation test below, a sensing sensor is configured as the aforementioned flow-cell sensor and the test is performed.

[Evaluation Test 1-1]

A sensing sensor is configured by using a substrate different from the substrate 21 of the above-described embodiment In the substrate, a layout of electrode films 27a to 27c is different from the layout shown in FIG. 4, and it is configured that thereby impedances from one end to the other end of the respective electrode films 27a to 27c become different from one another. After this sensing sensor is connected to an oscillation circuit unit 11 and pure water is first supplied as a sample solution, a glycerol 30% solution (viscosity coefficient is about 3.5%) diluted with pure water is supplied, and changes of frequencies F1, F2 of respective channels and a change of a frequency difference F1−F2 are investigated.

Figure 12:
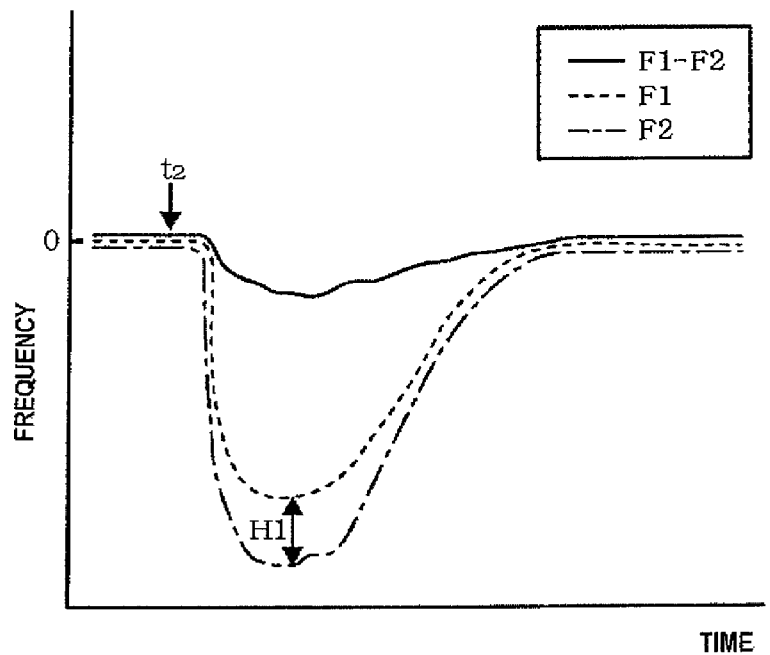
FIG. 12A and FIG. 12B are graphs showing states in which a frequency changes.
Figure 12:
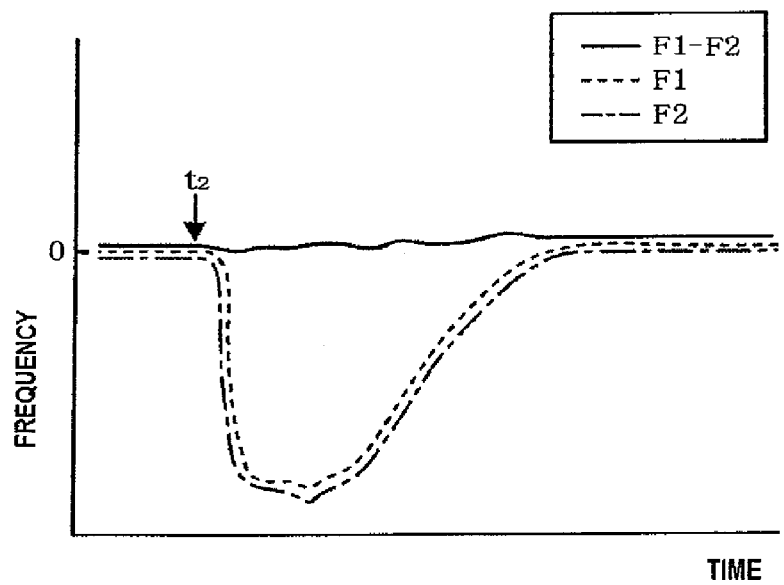

FIG. 12A is a graph showing a result of the above experiment. In the graph, a dotted line indicates F1, a chained line indicates F2, and a solid line indicates F1−F2, respectively. In this graph, values of the frequencies F1, F2 at a time that the pure water is supplied to the crystal piece 31 are 0 (zero). It should be noted that waveforms of the respective graph lines actually obtained are indicated in a manner to be slightly displaced vertically in order to make the graph viewable. In the graph, t2 indicates a point of time at which the glycerol 30% solution is supplied. As shown in this graph, falling amounts of F1, F2 after supply of the glycerol solution are not uniform, and a maximum value of a discrepancy amount between F1 and F2 indicated by H1 in the graph is 1000 Hz.

[Evaluation Test 1-2]

A test is performed under a condition similar to that of the evaluation test 1-1 except that the substrate 21 of the above-described embodiment is used. FIG. 12B is a graph showing a result of this experiment, and it is learned that a frequency F1 and a frequency F2 change similarly to each other. Accordingly, it is learned from the evaluation tests 1-1, 1-2 that in order to make falling amounts of respective crystal vibrators 3A, 3B uniform, equalizing impedances of respective conductive paths from an oscillation circuit 53 to excitation electrodes 32a, 32b is effective.

[Evaluation Test 2]

Figure 13:
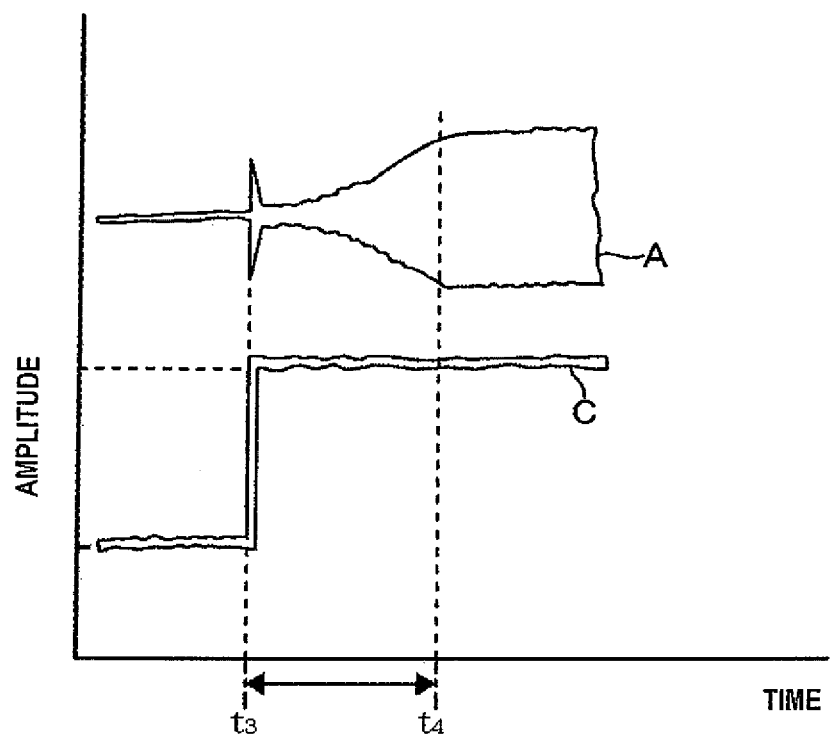
FIG. 13 is a graph showing an amplitude change of a frequency signal at a time of changeover of a switch.

In a sensing device 1, there are measured a frequency outputted from a channel 2 at a time that a connection of an oscillation circuit 53 changes over from a channel 1 to the channel 2 and a signal outputted from a switching signal output part 54 by an oscilloscope. FIG. 13 schematically shows waveforms obtained from a result of this experiment, C in a graph indicating the waveform of the switching signal and A in the graph indicating the output waveform of the channel 2, respectively. As shown in the graph of FIG. 13, an amplitude of the channel 2 is unstable from a time t3 at which an output level of the switching signal C changes until a time t4 thereafter.

A waveform of the channel 1 at a time that the connection of the oscillation circuit 53 changes over from the channel 2 to the channel 1 is also measured similarly. As a result, it is confirmed that immediately after change over of the output level of the switching signal the waveform is disordered similarly. Accordingly, it is learned that setting a period from the time t3 to the time t4 during which the frequency is unstable as a guard time during which the frequency is not measured as in the aforementioned embodiment is effective in performing measurement at a high accuracy.

[Evaluation Test 3-1]

A sensing sensor is formed similarly to in the evaluation test 1-1 by using a substrate in which a layout of electrode films 27a to 27c is different from that of FIG. 4 and in which it is configured thereby impedances from one end to the other end of the respective electrode films 27a to 27c are different from one another. Then, with regard to this sensing sensor, respective values of CI ($\Omega$), C0 (pF), C1 (fF), and L1 (mH) being crystal equivalent coefficients of the channel 1 and channel 2 are measured, and a difference between the channel 1 and the channel 2 is computed per each coefficient. Among computation results, a difference value of CI is −1.36Ω, and a difference value of C0 is 0.17 pF.

[Evaluation Test 3-2]

With regard to the sensing sensor of the above-described embodiment shown in FIG. 4, the respective values of CI (Ω), C0 (pF), C1 (fF), and L1 (mH) being crystal equivalent coefficients of the channel 1 and channel 2 are Measured similarly, and a difference between the channel 1 and the channel 2 is computed per each coefficient. When comparing the computed difference values between the sensing sensors, the difference value of CI is −0.80Ω and the difference value of C0 is 0.01 pF, and it is learned that differences of the values of CI and C0 in particular are suppressed between the channels, compared with the result of the evaluation test 3-1.

[Evaluation Test 4-1]

Pure water is supplied to the sensing sensor of the evaluation test 3-1, and subsequently a mixed solution of pure water and a 20% glycerol solution whose viscosity is higher than the pure water is supplied, and changes of frequencies F1, F2 and a frequency difference F1−F2 are measured similarly to in the evaluation test 1-1. Subsequently, pure water is supplied to the sensing sensor of the evaluation test 3-1, and subsequently a mixed solution of pure water and a 30% glycerol solution is supplied, and then changes of frequencies F1, F2 and a frequency difference F1−F2 are measured similarly to in the evaluation test 2.

Figure 14:
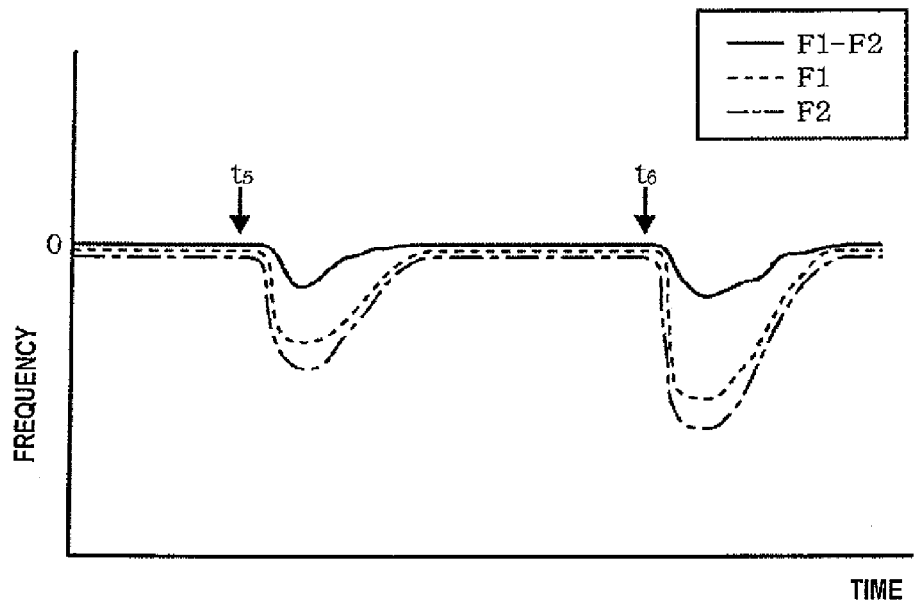
FIG. 14A and FIG. 14B are graphs showing states in which a frequency changes.
Figure 14:
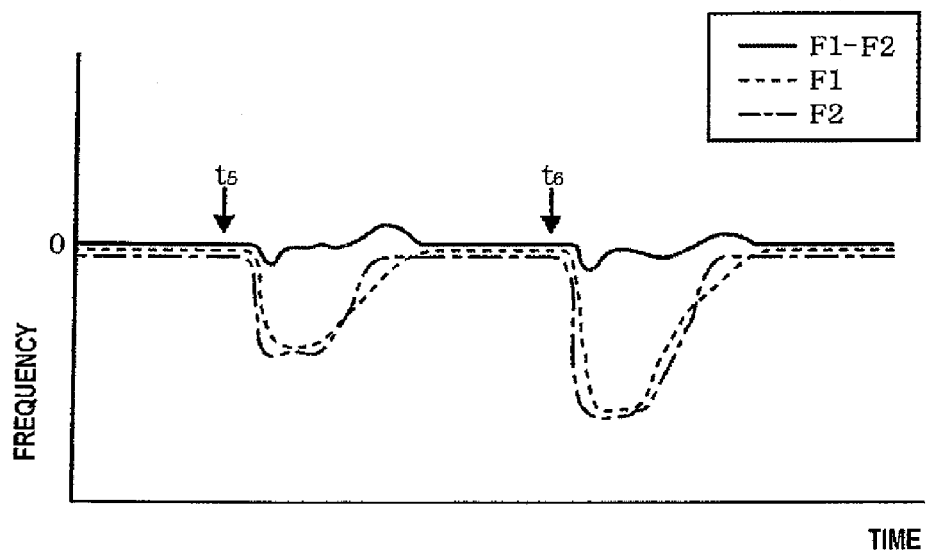
Figure 15:
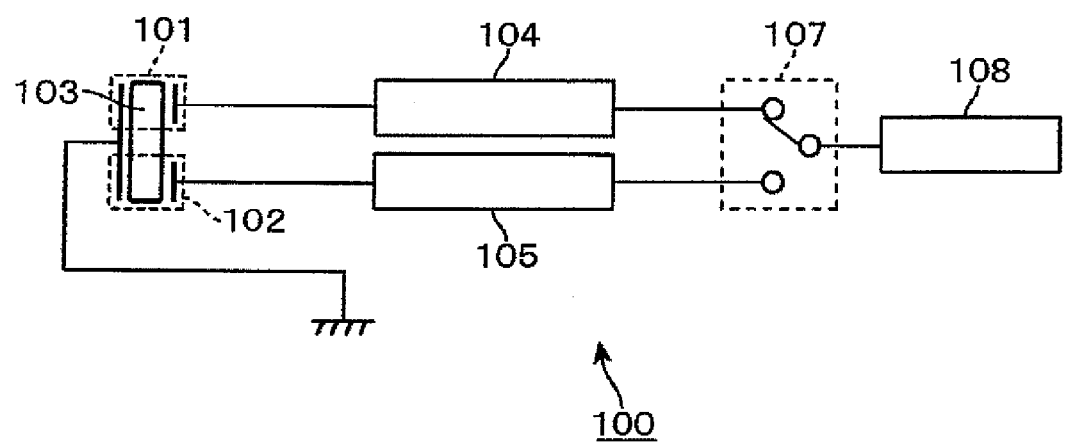
FIG. 15 is a block diagram showing a configuration of a conventional sensing device.

FIG. 14A shows a result of the evaluation test 4-1 by a graph similarly to in a case of the evaluation test 1-1. As shown in this graph, in the evaluation test 4-1, the difference between the oscillation frequencies F1, F2 emerges comparatively largely due to a viscosity of a sample solution. It should be noted that times t5 and t6 in the graph indicate timings of supplying of the 20% glycerol solution and of the 30% glycerol solution, respectively.

[Evaluation Test 4-2]

A test is performed similarly to in the case of the evaluation test 4-1, by using the sensing sensor 2 of the evaluation test 3-2. FIG. 14B indicates a result of this experiment. As shown in this graph, compared with the evaluation test 4-1, a difference between oscillation frequencies F1, F2 is small at a time of supplying of the 20% glycerol solution and 30% glycerol solution, respectively, and those oscillation frequencies change uniformly. It is learned from the results of the evaluation tests 3-1, 3-2, 4-1, and 4-2 that the impedance of the conductive path influences the C0 value and the CI value of the crystal equivalent coefficient and that the changes of the frequencies of the respective channels are not uniform due to the difference between the C0 value and the CI value between these channels. Further, it is indicated from the results of the evaluation tests 4-1 and 4-2 that making impedances of conductive paths uniform as in the present invention is effective in making a change of frequencies between channels uniform.

What is claimed is:

1. A sensing device using a piezoelectric vibrator whose characteristic vibration number changes by absorption of a substance to be sensed contained in a sample solution and sensing the substance to be sensed by a change of the characteristic vibration number, the sensing device comprising:

a first piezoelectric vibrator configured to be provided with a first one-surface-side excitation electrode on one of a front surface and a rear surface of a first vibration area provided in a piezoelectric piece and a first other-surface-side excitation electrode on the other, respectively, and configured that the substance to be sensed is absorbed;

a second piezoelectric vibrator configured to be provided with a second one-surface-side excitation electrode on one of a front surface and a rear surface of a second vibration area provided in the piezoelectric piece and a second other-surface-side excitation electrode on the other, respectively, and configured that the substance to be sensed is not absorbed;

a switching part switching the first one-surface-side excitation electrode and the second one-surface-side excitation electrode each other to connect to a subsequent stage side;

an oscillation circuit common to said first piezoelectric vibrator and said second piezoelectric vibrator, the oscillation circuit connected to the first other-surface-side excitation electrode and the second other-surface-side excitation electrode and provided in a subsequent stage of said switching part, and making said first piezoelectric vibrator and said second piezoelectric vibrator oscillate time-dividedly; and a measuring part provided in a subsequent stage of said oscillation circuit, and taking in outputs from said first piezoelectric vibrator and said second piezoelectric vibrator and measuring the characteristic vibration numbers of said first piezoelectric vibrator and said second piezoelectric vibrator, respectively, wherein an impedance of a conductive path including the first one-surface-side excitation electrode and an impedance of a conductive path including the second one-surface-side excitation electrode, when viewed from said oscillation circuit toward the first one-surface-side excitation electrode and the second one-surface-side excitation electrode, respectively, are uniform with each other, and wherein an impedance of a conductive path including the first other-surface-side excitation electrode and an impedance of a conductive path including the second other-surface-side excitation electrode, when viewed from said oscillation circuit toward the first other-surface-side excitation electrode and the second other-surface-side excitation electrode, respectively, are uniform with each other.

2. The sensing device according to claim 1, wherein the impedance of the conductive path and the impedance of the conductive path being uniform means that a difference between the impedances of the respective conductive paths is equal to or less than 3%.

3. The sensing device according to claim 1, wherein said switching part receives a switching signal outputted from a switching signal output part and changes over the connection of said first piezoelectric vibrator and said second piezoelectric vibrator to a subsequent stage side each other, and wherein said measuring part validates a measured value of the characteristic vibration number after passage of a time set in advance since the output of the switching signal.

* * * * *